(12) United States Patent
Fearnot et al.

(10) Patent No.: US 6,358,284 B1
(45) Date of Patent: Mar. 19, 2002

(54) TUBULAR GRAFTS FROM PURIFIED SUBMUCOSA

(75) Inventors: Neal E. Fearnot, West Lafayette; Michael C. Hiles, Lafayette, both of IN (US)

(73) Assignees: Med Institute, Inc.; Cook Biotech, Inc., both of West Lafayette, IN (US)

(*) Notice: Subject to any disclaimer, the term of this patent is extended or adjusted under 35 U.S.C. 154(b) by 0 days.

(21) Appl. No.: 09/324,989

(22) Filed: Jun. 2, 1999

Related U.S. Application Data

(63) Continuation of application No. PCT/US97/23006, filed on Dec. 10, 1997.
(60) Provisional application No. 60/032,679, filed on Dec. 10, 1996.

(51) Int. Cl.⁷ .................................................. A61F 2/36
(52) U.S. Cl. .................... 623/23.72; 623/1.44; 424/551
(58) Field of Search .............................. 623/23.72, 1.41, 623/1.44, 1.1; 424/551

(56) References Cited

U.S. PATENT DOCUMENTS

| | | | | |
|---|---|---|---|---|
| 2,127,903 A | * | 8/1938 | Bowen | |
| 3,562,820 A | * | 2/1971 | Braun | 623/1.41 |
| 4,502,159 A | | 3/1985 | Woodroof et al. | |
| 4,902,508 A | * | 2/1990 | Badylak et al. | 424/95 |
| 5,281,422 A | * | 1/1994 | Badylak et al. | 424/551 |
| 5,460,962 A | * | 10/1995 | Kemp | 435/238 |
| 5,788,625 A | * | 8/1998 | Plouhar et al. | 600/36 |
| 6,187,039 B1 | * | 2/2001 | Hiles et al. | 623/1.44 |
| 6,206,931 B1 | * | 3/2001 | Cook et al. | 623/23.75 |

FOREIGN PATENT DOCUMENTS

| | | |
|---|---|---|
| AU | 6481680 | 3/1982 |
| WO | 9631226 | 10/1996 |

\* cited by examiner

*Primary Examiner*—Paul B. Prebilic
(74) *Attorney, Agent, or Firm*—Woodard, Emhardt, Naughton, Moriarty & McNett

(57) ABSTRACT

An easy-to-produce and mechanically strong tube of an implantable graft prosthesis has been developed which is manufactured in any desired length, wall thickness, or diameter. The construct produced by the method of the invention may be used as grafts for arteries, veins, ureters, urethras, shunts, or in any application where a compliant, tissue-compatible tube is needed. The manufacture of the graft prosthesis generally involves wrapping multiple sheets of a purified, collagen-based matrix structure around a mandrel, compressing and drying the tissue on the mandrel before removing the construct for eventual use.

20 Claims, 3 Drawing Sheets

TUBULAR GRAFTS FROM PURIFIED SUBMUCOSA

CROSS-REFERENCES TO RELATED APPLICATIONS

This application is a continuation of international application Serial No. PCT/US97/23006, filed Dec. 10, 1997, designating the United States, which claims priority to U.S. Provisional Application Ser. No. 60/032,679, filed Dec. 10, 1996.

TECHNICAL FIELD

This invention relates to implantable graft constructs suitable for various medical applications and the process for producing such graft constructs. More specifically, purified submucosa is used to form tubular multi-laminate constructs of varying diameter. The graft constructs have applications as arterial and venous grafts, ureter and urethra replacements, and as various ducts and shunts.

BACKGROUND OF THE INVENTION

Researchers in the surgical arts have been working for many years to develop new techniques and materials for use as grafts to replace or repair damaged or diseased tissue structures, particularly bones and connective tissues, such as ligaments and tendons, and to hasten fracture healing. It is very common today, for instance, for an orthopedic surgeon to harvest a patellar tendon of autogenous or allogenous origin for use as a replacement for a torn cruciate ligament. The surgical methods for such techniques are well known. Further, it has become common for surgeons to use implantable prostheses formed from plastic, metal and/or ceramic materials for reconstruction or replacement of physiological structures. Yet, despite their wide use, presently available surgically implanted prostheses present many attendant risks to the patient. Therefore, surgeons are in need of a non-immunogenic, high tensile strength graft material which can be used for the surgical repair of bone, tendons, ligaments and other functional tissue structures.

More recently researchers have been working to develop biological tissues for use as implants and for use in the repair of damaged or diseased tissues, since plastic and polymer materials have drawbacks in these medical applications. While plastics and polymers may have some desirable mechanical properties (e.g., tensile strength), plastics have been found to become infected and in vascular applications plastics have been reported as inducing thrombogenesis.

Tubular prostheses made from natural tissues have been widely used in recent years in the surgical repair and replacement of diseased or damaged blood vessels in human patients. Natural tissue prostheses fall into three general classes: Autogenous, homologous, and heterologous prostheses. Autogenous material tissue prostheses are prepared from tissues taken from the patient's own body (e.g., saphenous vein grafts). Use of such prostheses eliminates the possibility of rejection of the implanted prosthesis, but requires a more extensive and time-consuming surgical intervention with attendant risks to the patient. Homologous natural tissue prostheses are prepared from tissue taken from another human, while heterologous natural tissue prosthesis are prepared from tissue taken from a different species. The use of homologous and heterologous umbilical cord vessels as, e.g., vascular and ureteral prostheses are disclosed in U.S. Pat. Nos. 3,894,530; 3,974,526; and 3,988,782.

In addition, autogenous vascular prostheses prepared from sheets of pericardial tissue have been disclosed by Yoshio Sako, "Prevention of Dilation in Autogenous Venous and Pericardial Grafts in the Thoracic Aorta," Surgery, 30, pp. 148–160 (1951) and by Robert G. Allen and Francis H. Cole, Jr., "Modified Blalock Shunts Utilizing Pericardial Tube Grafts," Jour. Pediatr. Surg., 12(3), pp. 287–294 (1977). Heterologous vascular prostheses prepared from sheets of porcine pericardial tissue have been disclosed by Ornvold K. et al., "Structural Changes of Stabilized Porcine Pericardium after Experimental and Clinical Implantation," in Proc. Eur. Soc. for Artif. Organs, Vol. VI, Geneva, Switzerland (1979).

The necessary characteristics of a tubular vascular prosthesis are biological compatibility, adequate strength, resistance to infection, resistance to biological degradation, non-thrombogenicity and lack of aneurysm formation. As used in this application, the term biological compatibility means that the prosthesis is non-toxic in the in vivo environment of its intended use, and is not rejected by the patient's physiological system (i.e., is non-antigenic). Furthermore, it is desirable that the prosthesis be capable of production at an economical cost in a wide variety of lengths, diameters and shapes (e.g., straight, curved, bifurcated), be readily anastomosed to the patient's body and to other tubular prostheses of the same or different type, and exhibit dimensional stability in use.

As disclosed in U.S. Pat. No. 4,902,508, vascular grafts constructs comprising intestinal submucosa have been previously described and utilized to replace damaged or diseased vascular tissues. More specifically, as disclosed in U.S. patent application Ser. No. 08/916,490, vascular grafts constructs comprising purified tela submucosa have been previously described and utilized to replace damaged or diseased vascular tissues. The vascular graft constructs were prepared by inserting a glass rod of the appropriate diameter into the lumen of the purified submucosa and hand-suturing along the seam of the purified submucosa. The purified submucosa vascular grafts are aseptically fabricated during surgery and typically take a surgeon about one half hour to prepare. Therefore to avoid spending time preparing the graft constructs during surgery, premade, presterilized grafts of different diameters are desirable.

Preparation of a tubular prosthesis of the correct length and shape increases the ease of implantation and enhances the functionality of the implant. For example, a tubular prosthesis that is too long for the intended application may kink after implantation, whereas implantation of a prosthesis that is too short places excessive tension on the anastomoses at its ends, thereby resulting in trauma to said anastomoses. Thus, it would be highly desirable to provide an array of tubular prostheses that vary in diameter and that can be cut transversely to a desired length at any point between its ends without otherwise substantially damaging the prosthesis.

The present invention is directed to a tubular prosthesis comprising purified submucosa and methods for preparing such a prosthesis. Purified submucosa, prepared in accordance with the present invention, has been previously described as a biocompatible, non-thrombogenic graft material that enhances the repair of damaged or diseased host tissues. Numerous studies have shown that warm-blooded vertebrate submucosa is capable of inducing host tissue proliferation, remodeling and regeneration of tissue structures following implantation in a number of in vivo microenvironments including lower urinary tract, body wall, tendon, ligament, bone, cardiovascular tissues and the central nervous system. Upon implantation, cellular infiltration and a rapid neovascularization are observed and the submucosa material is remodeled into host replacement tissue with site-specific structural and functional properties.

Purified submucosa can be obtained from various tissue sources, harvested from animals raised for meat production, including, for example, pigs, cattle and sheep or other warm-blooded vertebrates. More particularly, the purified submucosa is isolated from warm-blooded tissues including the alimentary, respiratory, urinary or genital tracts of warm-blooded vertebrates. In general purified submucosa is prepared from these tissue sources by delaminating the purified submucosa from both the smooth muscle layers and the mucosal layers. The preparation of intestinal submucosa is described and claimed in U.S. Pat. No. 4,902,508, and the preparation of tela submucosa is described and claimed in U.S. patent application Ser. No. 08/916,490, the disclosure of which is expressly incorporated herein by reference.

SUMMARY OF THE INVENTION

In accordance with the present invention, an implantable tubular prosthesis comprising purified submucosa is prepared in the shape of a tube. The tubular construct comprises a first sheet of purified submucosa and, optionally, rolled into the shape of a multi-layered tube of purified submucosa and a second sheet of purified submucosa that is wrapped around the tube of purified submucosa. The second sheet of purified submucosa is overlaid onto the tube of purified submucosa so that a first edge is in contact with the purified submucosa and the second opposite edge is either sutured to the first edge or extends over the first edge and is sutured to the second sheet of purified submucosa. The multi-layered tubular graft constructs of the present invention are formed to have fluid-tight seams and can be shaped to match the endogenous tissue to be replaced by the graft construct.

Further in accordance with the present invention, a process is provided for producing an implantable graft construct formed in the shape of a tube having a seam extending longitudinally along the length of the graft wherein the seam has been sealed to resist movement of fluids from the lumen through the seam to the exterior of the tube. The method of forming the purified submucosal tubular constructs of the present invention comprises the steps of:

A. overlaying a sheet of purified submucosa around the circumference of a mandrel to form a tube of purified submucosa having a multi-layered overlapped region;

B. fixing the purified submucosa layers in the overlapped region to one another;

C. (optionally) overlaying a second sheet of purified submucosa onto the tube of purified submucosa to form a second tube of purified submucosa wherein the seam of the second tube of purified submucosa is sealed by sutures; and D. compressing the layers of purified submucosa under dehydrating conditions.

The present invention allows for the construction of multi-layered tubular graft constructs from sheets of purified submucosa wherein the walls of the formed tubular prosthesis do not contain any perforations that provide a direct passageway from the lumen of the tube to the exterior surface. The multi-layered tubular prostheses of the present invention have sufficient strength and durability to be used in vascular applications without leakage or failure of the tubular prosthesis.

BRIEF DESCRIPTION OF THE DRAWINGS

The invention will be further described in connection with the attached drawing figures showing preferred embodiments of the invention including specific parts and arrangements of parts. It is intended that the drawings included as a part of this specification be illustrative of the preferred embodiments of the present invention and should in no way be considered as a limitation on the scope of the invention.

DETAILED DESCRIPTION

Figure 1:
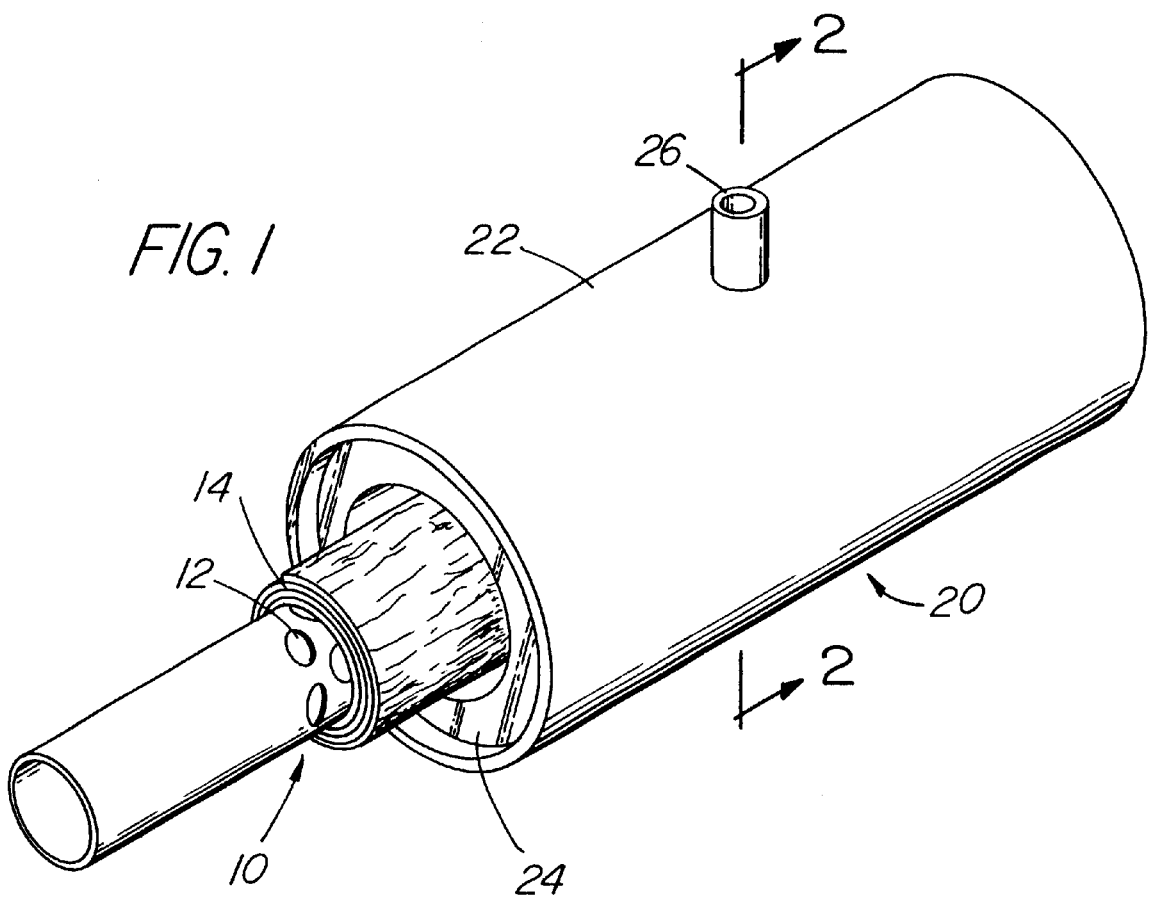
FIG. 1 is a sectional view of a compression chamber with a purified submucosa covered mandrel inserted into the lumen of the compression chamber.

In many medical applications, an implantable, biocompatible tubular prosthesis is desirable. In general, the present invention provides an arbitrary length, arbitrary diameter, multi-layer graft construct. The product can be manipulated to suit various medical applications where a tubular construct or conduit is desired. Examples of possible applications are arterial and venous grafts, ureter and urethra replacements, and various ducts and shunts. The process of fabricating the tubular constructs of the present invention involves preparing a sheet of purified submucosa in accordance with U.S. patent application Ser. No. 08/916,490, and overlaying the matrix structure around a mandrel of the appropriate diameter to form a tube of purified submucosa. The sheet of purified submucosa can be wrapped around the mandrel multiple times, to form a multi-layered tube of purified submucosa. A second sheet of purified submucosa is then wrapped around the circumference of the formed tube of purified submucosa and the end of the second sheet of purified submucosa is sutured to the graft construct to form a water tight seam that extends longitudinally along the length of the tube. The purified submucosa is then compressed under dehydrating conditions, and optionally heated, to produce the unitary tubular prosthesis of the present invention.

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

In the discussions herein, a number of terms are used. In order to provide and clear and consistent understanding of the specification and claims, the following definitions are provided.

Bioburden—refers to the number of living microorganisms, reported in colony-forming units (CFU), found on and/or in a given amount of material. Illustrative microorganisms include bacteria, fungi and their spores.

Disinfection—refers to a reduction in the bioburden of a material.

Sterile—refers to a condition wherein a material has a bioburden such that the probability of having one living microorganism (CFU) on and/or in a given section of the material is one in one-million or less.

Pyrogen—refers to a substance which produces febrile response after introduction into a host.

Endotoxin—refers to a particular pyrogen which is part of the cell wall of gram-negative bacteria. Endotoxins are continually shed from the bacteria and contaminate materials.

Purification—refers to the treatment of a material to remove one or more contaminants which occur with the material, for instance contaminants with which the material occurs in nature, and/or microorganisms or components thereof occurring on the material. Illustratively, the contaminants may be those known to cause toxicity, infectivity, pyrogenicity, irritation potential, reactivity, hemolytic activity, carcinogenicity and/or immunogenicity.

Biocompatibility—refers to the ability of a material to pass the Biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests assay as to a material's toxicity, infectivity, pyrogenicity, irritation potential, reactivity, hemolytic activity, carcinogenicity and/or immunogenicity. A biocompatible structure or material when introduced into a majority of patients will not cause an adverse reaction or response. In addition, it is contemplated that biocompatibility can be effected by other contaminants such as prions, surfactants, oligonucleotides, and other biocompatibility effecting agents or contaminants.

Contaminant—refers to an unwanted substance on, attached to, or within a material. This includes, but is not limited to: bioburden, endotoxins, processing agents such as antimicrobial agents, blood, blood components, viruses, DNA, RNA, spores, fragments of unwanted tissue layers, cellular debris, and mucosa.

Tela submucosa—refers to a layer of collagen-containing connective tissue occurring under the mucosa in most parts of the alimentary, respiratory, urinary and genital tracts of animals.

As disclosed above, the present invention generally provides graft prostheses and materials including a purified collagen-based matrix structure, and methods for obtaining and using the same. Advantageous graft prostheses of the invention are obtained from a submucosa tissue source, for example including animal tissues such as human or other mammalian tissues, e.g. porcine, bovine or ovine tissues.

Tela submucosa, as with many animal tissues, is generally aseptic in its natural state, provided the human or animal does not have an infection or disease. This is particularly the case since the tela submucosa is an internal layer within the alimentary, respiratory, urinary and genital tracts of animals. Accordingly, it is generally not exposed to bacteria and other cellular debris such as the epithelium of the intestinal tract. One feature of the present invention is the discovery that by disinfecting the source tissue for the tela submucosa prior to delamination, the aseptic state of the tela submucosa layer can be preserved or substantially preserved, particularly if the delamination process occurs under sterile conditions.

In particular, it has been discovered that disinfecting the tela submucosa source, followed by removal of a purified matrix including the tela submucosa, e.g. by delaminating the tela submucosa from the tunica muscularis and the tunica mucosa, minimizes the exposure of the tela submucosa to bacteria and other contaminants. In turn, this enables minimizing exposure of the isolated tela submucosa matrix to disinfectants or sterilants if desired, thus substantially preserving the inherent biochemistry of the tela submucosa and many of the tela submucosa's beneficial effects.

A tela submucosa implantable collagen matrix according to the present invention can, as indicated above, be obtained from the alimentary, respiratory, urinary or genital tracts of animals. Preferably, the tela submucosa tissues, which are collagen-based and thus predominantly collagen, are derived from the alimentary tract of mammals and most preferably from the intestinal tract of pigs. A most preferred source of whole small intestine is harvested from mature adult pigs weighing greater than about 450 pounds. Intestines harvested from healthy, nondiseased animals will contain blood vessels and blood supply within the intestinal tract, as well as various microbes such as *E. coli* contained within the lumen of the intestines. Therefore, disinfecting the whole intestine prior to delamination of the tela submucosa substantially removes these contaminants and provides a preferred implantable tela submucosa tissue which is substantially free of blood and blood components as well as any other microbial organisms, pyrogens or other pathogens that may be present. In effect, this procedure is believed to substantially preserve the inherent aseptic state of the tela submucosa, although it should be understood that it is not intended that the present invention be limited by any theory.

It is also desirable that the collagen matrix according to the present invention be substantially free of any antibiotics, antiviral agents or any antimicrobial type agents which may affect the inherent biochemistry of the matrix and its efficacy upon implantation. In the past, one method of treating such matrix structure is to rinse the delaminated matrix in saline and soak it in an antimicrobial agent, for example, as disclosed in U.S. Pat. No. 4,956,178. While such techniques can optionally be practiced with isolated submucosa of the present invention, preferred processes according to present invention avoid the use of antimicrobial agents and the like which may not only affect the biochemistry of the collagen matrix but also can be unnecessarily introduced into the tissues of the patient.

As discussed above, it has been discovered that a highly pure form of an implantable tela submucosa collagen matrix may be obtained by first disinfecting a tela submucosa source prior to removing a purified collagen matrix including the tela submucosa layer, e.g. by delaminating the tela submucosa source. It has also been discovered that certain processing advantages as well as improved properties of the resultant tela submucosa layer are obtained by this process, including greater ease in removing attached tissues from the submucosa layer, and a characteristic, low contaminant profile.

Purified submucosa suitable for use in the formation of the present graft constructs comprises naturally associated extracellular matrix proteins, glycoproteins and other factors. Purified submucosas for use in accordance with this invention include purified intestinal submucosa, purified stomach submucosa, purified urinary bladder submucosa, and purified uterine submucosa. Purified intestinal submucosa is one preferred material, and more particularly purified small intestinal submucosa.

The preparation of submucosa is described in U.S. Pat. No. 4,902,508, and, more particularly, the preparation of purified submucosa for use in accordance with the present invention is described in U.S. patent application Ser. No. 08/916,490 filed Aug. 22, 1997, titled "Graft Prosthesis, Materials and Methods" which claims priority to and incorporates herein by reference Ser. No. 60/024,693, filed Sep. 9, 1996, titled "A Highly Purified Tela Submucosa Implantable Tissue," and Ser. No. 60/024,542, filed Aug. 23, 1996, titled "A Substantially Purified Tela Submucosa Implantable Tissue."

As a tissue graft, purified submucosa undergoes remodeling and induces the growth of endogenous tissues upon implantation into a host. It has been used successfully in vascular grafts, urinary bladder and hernia repair, replacement and repair of tendons and ligaments, and dermal grafts. When used in such applications, the graft constructs appear not only to serve as a matrix for the regrowth of the tissues replaced by the graft constructs, but also promote or induce such regrowth of endogenous tissue. Common events to this remodeling process include: widespread and very rapid neovascularization, proliferation of granulation mesenchymal cells, biodegradation/resorption of implanted purified intestinal submucosa material, and lack of immune rejection.

The tubular purified submucosa graft constructs of the present invention can be sterilized using conventional sterilization techniques including glutaraldehyde tanning, formaldehyde tanning at acidic pH, propylene oxide or ethylene oxide treatment, gas plasma sterilization, gamma radiation, electron beam, and peracetic acid sterilization. Sterilization techniques which do not adversely affect the mechanical strength, structure, and biotropic properties of the purified submucosa is preferred. For instance, strong gamma radiation may cause loss of strength of the sheets of purified submucosa. Preferred sterilization techniques include exposing the graft to peracetic acid, 1–4 Mrads gamma irradiation (more preferably 1–2.5 Mrads of gamma irradiation), ethylene oxide treatment or gas plasma sterilization; peracetic acid sterilization is the most preferred sterilization method. Typically, the purified submucosa is subjected two or more sterilization processes. After the purified submucosa is sterilized, for example by chemical treatment, the matrix structure may be wrapped in a plastic or foil wrap and sterilized again using electron beam or gamma irradiation sterilization techniques.

Purified submucosa can be stored in a hydrated or dehydrated state. Lyophilized or air dried purified submucosa can be rehydrated and used in accordance with this invention without significant loss of its biotropic and mechanical properties.

The sheets of purified submucosa can be conditioned, as described in U.S. patent application Ser. No. 08/916,490, to alter the viscoelastic properties of the purified submucosa. In accordance with one embodiment purified submucosa delaminated from the tunica muscularis and luminal portion of the tunica mucosa is conditioned to have a strain of no more than 20%. The purified submucosa is conditioned by stretching, chemically treating, enzymatically treating or exposing the matrix structure to other environmental factors. In one embodiment the strips of purified tela submucosa are conditioned by stretching in a longitudinal or lateral direction so that the strips of purified tela submucosa have a strain of no more than 20%.

In one embodiment the purified submucosa is conditioned by stretching the graft material longitudinally to a length longer than the length of the purified submucosa from which the graft construct was formed. One method of conditioning the matrix by stretching involves application of a given load to the purified submucosa for three to five cycles. Each cycle consists of applying a load to the graft material for five seconds, followed by a ten second relaxation phase. Three to five cycles produces a stretch-conditioned graft material with reduced strain. The graft material does not immediately return to its original size; it remains in a "stretched" dimension. Optionally, the graft material can be preconditioned by stretching in the lateral dimension.

In one embodiment the purified submucosa is stretched using 50% of the predicted ultimate load. The "ultimate load" is the maximum load that can be applied to the purified submucosa without resulting in failure of the matrix structure (i.e., the break point of the tissue). Ultimate load can be predicted for a given strip of purified submucosa based on the source and thickness of the material. Accordingly, one method of conditioning the matrix structure by stretching involves application of 50% of the predicted ultimate load to the purified submucosa for three to ten cycles. Each cycle consists of applying a load to the graft material for five seconds, followed by a ten second relaxation phase. The resulting conditioned purified submucosa has a strain of less than 30%, more typically a strain from about 20% to about 28%. In one preferred embodiment conditioned the purified submucosa has a strain of no more than 20%. The term strain, as used herein, refers to the maximum amount of matrix elongation before failure of the matrix, when the matrix is stretched under an applied load. It is expressed as a percentage of the length of the matrix before loading. The conditioned purified submucosa strips can be used to form the tubular construct or alternatively the tubular construct can be conditioned after its formation.

The tubular graft constructs of the present invention are formed as a multilaminate construct wherein a first sheet of purified submucosa is formed into the shape of a tube of purified submucosa and, optionally, a second sheet is overlaid onto the tube of purified submucosa. The dimensions of the individual sheets of purified submucosa used is not critical and the term "sheet of purified submucosa" is defined herein to include purified submucosa from one or more vertebrate sources or organs in a wide variety of sizes and shapes. After the second sheet of purified submucosa has been layered onto the mandrel, pressure is applied to the overlapped portions to compress the purified submucosal against the mandrel. In preferred embodiments the mandrel surfaces is water permeable. The term "water permeable surface" as used herein includes surfaces that are water absorbent, microporous or macroporous. Macroporous materials include perforated plates or meshes made of plastic, metal, ceramics or wood.

In one preferred embodiment the multiple layers of purified submucosa are compressed under dehydrating conditions. The term "dehydrating conditions" is defined to include any mechanical or environmental condition which promotes or induces the removal of water from the purified submucosa. To promote dehydration of the compressed purified submucosa, at least one of the two surfaces compressing the matrix structure is water permeable. Dehydration of the matrix structure can optionally be further enhanced by applying blotting material, heating the matrix structure or blowing air across the exterior of the compressing surfaces.

Purified submucosa typically has an abluminal and a luminal surface. The luminal surface is the purified submucosal surface facing the lumen of the organ source and typically adjacent to an inner mucosa layer in vivo whereas the abluminal surface is the purified submucosal surface facing away from the lumen of the organ source and typically in contact with smooth muscle tissue in vivo. In one embodiment one or more sheets of purified submucosa are wrapped onto the mandrel with the luminal surface of the purified submucosa in contact with the mandrel surface. Thus the luminal surface of the sheet of purified submucosa faces the lumen of the formed tube of purified submucosa. However the tube of purified submucosa can also be formed from one or more sheets of purified submucosa with the abluminal surface facing the lumen of the formed tubular graft construct.

In accordance with one embodiment a tubular prosthesis is manufactured comprising a first sheet of purified submucosa formed in the shape of a tube of purified submucosa, and a second sheet of purified submucosa circumferentially wrapped around the tube of purified submucosa, wherein the free end of the second sheet of purified submucosa is sutured to the wrapped purified submucosa. The tube of purified submucosa comprises the first sheet of purified submucosa, having a first edge and a second opposite edge, formed in the shape of a tube wherein the second opposite edge of the first sheet extends over the first edge of the first sheet to define a multiple layered overlapped region of purified submucosa. As used herein the term "overlapped region" refers to the portion of the multilayered tube defined by an overlap angle ($\theta$) that extends between the first and second edges of the first sheet of purified submucosa formed as a tube (see FIG. 6). The purified submucosa layers in the overlapped region are fixed to one another using standard techniques known to those skilled in the art.

In one embodiment the multiple layers of purified submucosa in the overlapped region are fixed to one another by treatment with a cross-linking agent, for example an aldehyde such as formaldehyde or more preferably glutaraldehyde. In one embodiment the seam of the wrapped tube of purified submucosa can be "spot welded" to ensure that the end piece does not come loose. In accordance with this embodiment, a Q-tip, moistened with X % glutaraldehyde (or other cross-linking or adhesive agent), is wiped along the overlapped region forming the seam. The value for X is about 0.1 to about 1.0%, more probably about 0.5%, but there is a relationship between the seam width, the glutaraldehyde concentration and number of turns that determines the bursting pressure. In one embodiment the entire graft construct can be immersed into a solution of glutaraldehyde to fix the multiple layers of the tube of purified submucosa to one another. In addition, the multiple layers of purified submucosa in the overlapped region can be sutured to one another, and in one embodiment the layers of the overlapped region are fixed with sutures in the absence of treatment with a cross-linking agent.

Figure 6:
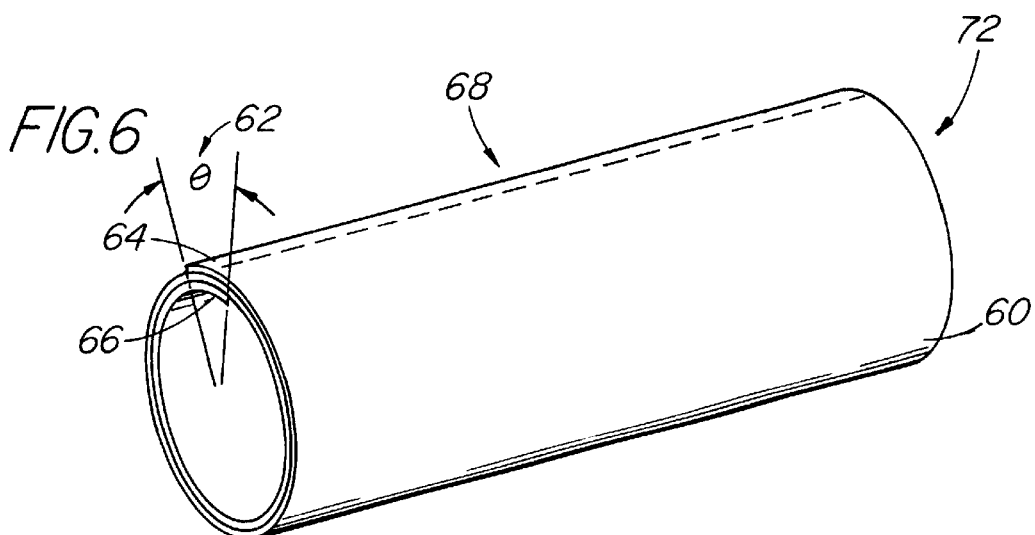
FIG. 6 is a perspective view of a multihole mandrel having been wrapped with a single strip of water permeable material, and a first sheet of purified submucosa.

In one preferred embodiment the tube of purified submucosa formed by the first sheet of purified submucosa is formed such that the first and second opposite edges of the first sheet of purified submucosa are substantially parallel to one another as shown in FIG. 6. In this embodiment the sheet of purified submucosa is rolled into the shape of a tube having multiple layers. Typically the tube of purified submucosa comprises two layers of purified submucosa and the multiple overlapped region comprises three layers of purified submucosa.

The graft constructs of the present invention may further comprise a second sheet of purified submucosa wherein the second sheet is in adherent contact with the exterior surface of the tube of purified submucosa. In one embodiment, the first and second opposite edges of the second sheet of purified submucosa are sutured together along the length of the tube of purified submucosa without perforating the underlying tube of purified submucosa. In an alternative embodiment, the second opposite edge of the second sheet extends over the first edge of the second sheet and is sutured to the second sheet of purified submucosa without perforating the underlying tube of purified submucosa.

In preferred embodiments, the overlapped region of the tube of purified submucosa is offset from the sutures formed in the second sheet in purified submucosa. In one embodiment the sutures formed in the second sheet of purified submucosa are situated 90–180° along the circumference of the tube of purified submucosa in relation to the overlapped region, and in one embodiment the sutures are located 180° along the circumference of the tube of purified submucosa in relation to the overlapped region (See FIG. 7).

In accordance with one embodiment, the tubular prosthesis comprises a first sheet of purified submucosa, having first and second edges that are substantially parallel to each other, rolled into the shape of a multi-layered tube having an overlapped region wherein the first and second edges remain substantially parallel to one another in the formed tube and the layers of the overlapped region are fixed ton one another with sutures or by exposure to a cross-linking agent. The tubular construct further comprises a second sheet of purified submucosa adhered to the exterior surface of the formed tube of purified submucosa, wherein the second sheet, having first and second edges that are substantially parallel to each other, is wrapped circumferentially around the tube of purified submucosa and the first and second edges are fixed to one another with sutures.

In accordance with one embodiment the tubular prosthesis of the present invention is formed by the following steps: A mandrel is selected having a diameter matching the preferred diameter of the final construct. The mandrel is typically cylindrical in shape and in preferred embodiments comprises a hollow tube that is water permeable. A first sheet of purified submucosa, having a first edge and a second opposite edge, is then overlaid onto the mandrel to form a tube of purified submucosa, wherein the second opposite edge of the first sheet of purified submucosa extends over the first edge of the first sheet of purified submucosa to define a multi-layered overlapped region of purified submucosa. The purified submucosa layers in the overlapped region are then fixed to one another to form a seam that extends longitudinally along the length of the formed tube. A second sheet of purified submucosa, having a first edge and a second opposite edge is then overlaid onto the tube of purified submucosa and the second opposite edge of the second sheet of purified submucosa is sutured to the overlaid second sheet of purified submucosa along the length of the tube of purified submucosa without perforating the tube of purified submucosa. In one embodiment the first and second edges of the second sheet of purified submucosa are sutured together to form a single layered second tube that encompassed the first tube of purified submucosa. The layers of purified submucosa are then compressed against the mandrel under dehydrating conditions.

In one preferred embodiment of preparing the tubular constructs of the present invention (See FIG. 5), the mandrel 50 is first covered with a removable strip of water permeable material 52 before the first sheet of purified submucosa is overlaid onto the mandrel. After formation of the tubular prosthesis, the strip of water permeable material is removed from the mandrel to assist in the release of the tubular prosthesis from the mandrel.

Figure 5:
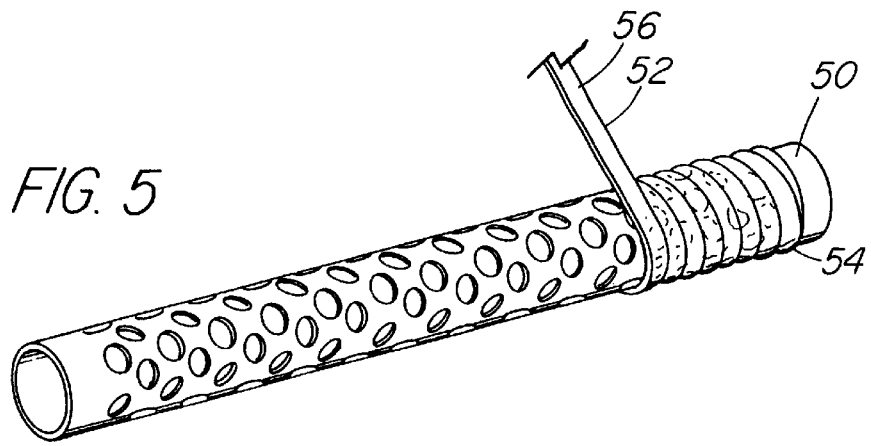
FIG. 5 is a perspective view of a single strip of water permeable material wound around a multihole mandrel.
Figure 7:
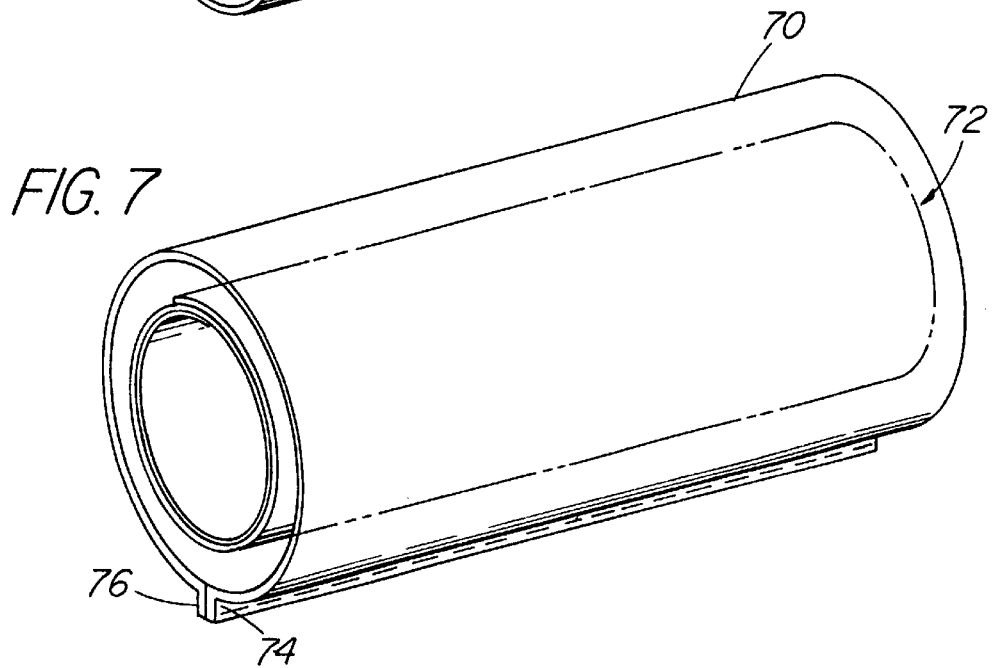
FIG. 7 is a perspective view of a multihole mandrel having been wrapped with a single strip of water permeable material, a first sheet of purified submucosa and a second sheet of purified submucosa.

In accordance with one embodiment, as shown in FIG. 5–FIG. 7 the method of forming the construct comprises selecting a water permeable, hollow mandrel 50 of appropriate diameter, and spiral wrapping the mandrel with a strip of water permeable material 52, for example umbilical tape. Then the desired number of wraps of a first sheet of purified submucosa 60 are applied wherein a "wrap of purified submucosa" is defined as a piece of purified submucosa wrapped 360° about the mandrel. Typically 1 or 2 wraps provide a burst strength of about 1000–2000 mmHg after fabrication as described below. The purified submucosa is applied to the mandrel 50 by a rolling motion with the desired number of layers (typically two) and an overlapped region 62 (defined by an overlap angle (θ) of about 30 degrees extending between the first edge 64 and second edges 66 of the purified submucosa) to form a tube of purified submucosa 72 having a longitudinally extending seam 68, as shown in FIG. 6.

In one embodiment, the seam of the wrapped purified submucosa can be "spot welded" to ensure that the end piece does not come loose. In accordance with this embodiment, a Q-tip, moistened with X % glutaraldehyde (or other cross-linking or adhesive agent), is wiped along the overlap which is the seam. The value for X is about 0.1 to about 1.0%, more probably about 0.5%, but there is a relationship between the seam width, the glutaraldehyde concentration and number of turns that determines the bursting pressure. The seam can also be cross-linked to ensure that the end piece does not come loose by immersing the entire tube of purified submucosa in a solution of a cross-linking agent such as glutaraldehyde. The glutaraldehyde treated tube of purified submucosa can be optionally compressed under dehydrating conditions before overlaying the second sheet of purified submucosa over the tube of purified submucosa, including the use of vacuum pressing, to further bond the layers of purified submucosa to one another.

In another embodiment, the seam of purified submucosa tube can be spot welded with a laser to further seal the seam and bond the matrix structure into a unitary tube of purified submucosa.

Alternatively, the seam of the tube of purified submucosa can be fixed by suturing the multiple layers of the tube of purified submucosa along the overlapped region. The use of sutures negates the need for cross-linking the seam of the purified submucosa. In one preferred embodiment, the method of preparing a tubular prosthesis comprising purified submucosa comprises overlaying a first strip of water permeable material about the circumference of a mandrel and then overlaying a second strip of water permeable material on top of the first strip of water permeable material. A first sheet of purified submucosa, having a first edge and a second opposite edge, is then overlaid onto the spirally wrapped material to form a tube of purified submucosa, wherein the second opposite edge extends over the first edge to define a multi-layered overlapped region of purified submucosa. The tube of purified submucosa is then compressed against the surface of the mandrel under dehydrating conditions to form a tube-shaped construct. The second strip of the water permeable material is then removed from the mandrel to release the tube-shaped construct from the mandrel. The overlapped region of the released tube of purified submucosa is sutured, using a continuous suture to ensure that the tube will not unravel. The tube-shaped construct is then returned to the mandrel and slid over the first strip of water permeable material covering the mandrel. A second sheet of purified submucosa, having a fist edge and a second opposite edge, is then overlaid onto the first sheet of purified submucosa. The first and second opposite edges of the second sheet of purified submucosa are sutured together along the length of the tube of purified submucosa without perforating the tube of purified submucosa, and the first strip of water permeable material is removed from the mandrel to release the tubular prosthesis from the mandrel. In preferred embodiments, the sutures of the second sheet of purified submucosa do not overlap the sutures formed in the tube of purified submucosa.

After formation of the tube of purified submucosa, a second sheet of purified submucosa 70 is then wrapped circumferentially around the exterior surface of the formed tube of purified submucosa 72. In one embodiment, the second sheet of purified submucosa 70 is overlaid onto the tube of purified submucosa 72, wrapped about the tube once, and the first edge 74 and the second opposite edge 76 of the second sheet of purified submucosa are sutured together along the length of the tube of purified submucosa without perforating the tube of purified submucosa (See FIG. 7). Alternatively, the second sheet of purified submucosa is overlaid onto the tube of purified submucosa, wrapped about the tube at least once wherein the second opposite edge of the second sheet extends over the first edge of the second sheet of purified submucosa and said second opposite edge of the second sheet is sutured along the length of the tube of purified submucosa without perforating the tube of purified submucosa.

After the mandrel has been wrapped with the second sheet of purified submucosa, the purified submucosa is compressed under dehydrating conditions. In one embodiment, the matrix structure is vacuum pressed, wherein one end of the mandrel is closed and the interior of the purified submucosa-covered mandrel is connected to a vacuum pump. The vacuum causes atmospheric pressure to compress the purified submucosa layers, and in those embodiments that use a cross-linking agent to cross-link the purified submucosa layers to one another, the vacuum pressing procedure causes the cross-linking agent to penetrate the entire thickness of the seam. The vacuum sealing/drying process is completed typically in about four hours.

After the drying/sealing treatment, the ends of the umbilical tape are grasped and pulled longitudinally. The tape unwinds easily under the purified submucosa tube which then slides off the mandrel easily. The result is a seamless tube that looks like a soda-pop straw.

In accordance with the present invention the purified submucosa can be wrapped onto the mandrel in a variety of different orientations. In one embodiment the sheets have a width equal to the length of the mandrel such that a single sheet entirely covers the mandrel when wrapped 360° around the mandrel (See FIG. 4).

Figure 3:
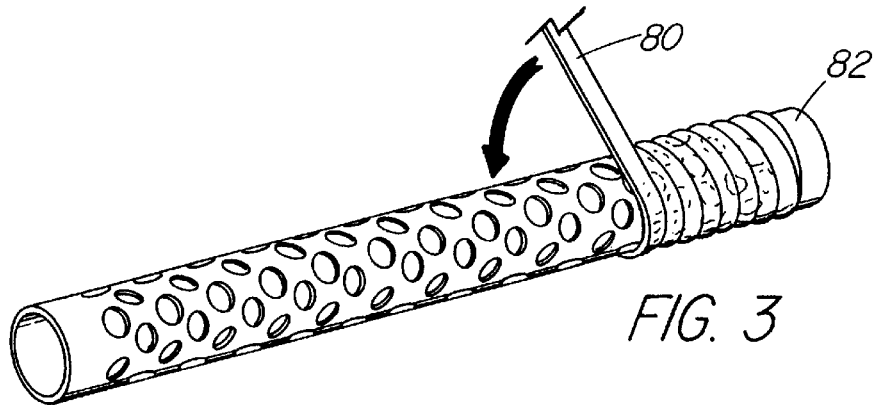
FIG. 3 is a perspective view of a single strip of purified submucosa helically wound around the mandrel.

Other wrapping techniques can be used to form the first sheet of purified submucosa into the tube of purified submucosa provided that no gaps exist between the seams of overlapped layers. In one embodiment, the sheet of purified submucosa may have a width less than the length of the mandrel. In this alternative embodiment the sheet of purified submucosa 80 must be wound about the mandrel 82 multiple times wherein the sheet is at least partially overlapped leaving no portion of the underlying mandrel exposed (See FIG. 3). The amount of overlap in such partially overlapped sheets of purified submucosa ranges between 10–60% of the width of the individual sheet and more preferably the overlapped portion is a 50% overlap. In one embodiment multiple pieces of purified submucosa can be overlaid onto the mandrel, provided that at least a portion of each piece of purified submucosa overlaps a portion of another piece of purified submucosa wrapped onto the mandrel. In a further embodiment, a long, narrow sheet of purified submucosa can be spirally wrapped on the mandrel with an overlap, followed by a spiral wrapping in the opposite direction. This will provide 4 layers of purified submucosa to support the internal pressure. In this embodiment, seams formed by overlapped sheets of purified submucosa should overlap by 0.5 to 3 cm and more preferably from 1 to 2 cm. In the embodiments where the first sheet of purified submucosa used to form the tube of purified submucosa has a width less then the length of the mandrel the seams of the tube will be fixed by exposure to a cross-linking agent.

In addition, when the second sheet of purified submucosa is overlaid onto the tube of purified submucosa formed from the first sheet of purified submucosa, the second sheet can be overlaid with its abluminal surface or its luminal surface in contact with the tube of purified submucosa. Each of these combinations of overlapping the sheets of purified submucosa from the same or different vertebrate or organ sources will produce a unitary tubular shape purified submucosa graft construct upon compression of at least the overlapped portions under conditions allowing dehydration of the matrix structure.

The invention will be further described with respect to preferred embodiments as illustrated in the drawing figures. Referring to FIG. 1, one preferred embodiment of a mandrel 10 for wrapping matrix structure sheets is illustrated. The mandrel 10 is a hollow metal or plastic tube comprising holes 12 in the wall of the tube along a portion of, or, alternatively, along the entire length of the metal tube. The size of the holes in the mandrel 10 is not critical provided the mandrel is sufficiently porous to allow dehydration of the purified submucosa upon compression of the matrix structure 14. In one preferred embodiment the mandrel is a metal tube, and more preferably, the metal tube is composed of aluminum. Purified submucosa 14 is overlaid onto the mandrel 10 to form a multi-layered tube of purified submucosa.

Figure 2:
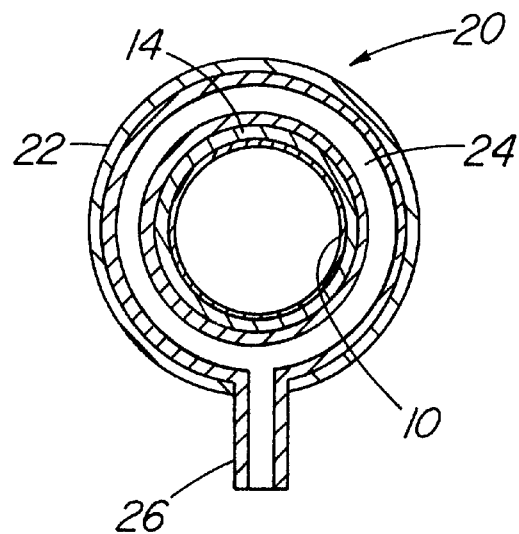
FIG. 2 is a perspective view of the compression chamber of claim 1.

The purified submucosa covered mandrel is then inserted into the luminal space of a compression chamber 20 that is utilized in one embodiment to prepare the tubular constructs of the present invention. The compression chamber 20 comprises outer shell 22, a bladder 24 and pressure port 26. The bladder 24 may be attached or adhered to the inner wall of outer shell 22 by various techniques, e.g., with an adhesive or heat bonding. As shown in FIG. 2, the wrapped mandrel 10 is inserted into compression chamber 20 where inner membrane 24 contacts and compresses the purified submucosa 14 when a fluid is delivered into pressure port 26 to inflate membrane 24. Bladder 24 is inflated to desired pressure and the pressure is maintained until the purified submucosa has been sufficiently dehydrated.

Optionally, the compression and drying process may be augmented with low temperature heating (e.g., less than about 50° C.) of the graft construct. Further, air or an inert gas (e.g., $N_2$) may be passed through the lumen of the mandrel as an alternative or conjunctive means to augment the drying process. The air/gas drawn through the lumen can optionally be heated to further speed the dehydration process. The holes 12 formed in the walls of mandrel 10 aid in the drying process of matrix structure sheets 14 and, therefore, this structure merely represents a preferred embodiment of the present invention (see FIG. 1). Accordingly, the mandrel can be formed as a solid cylinder. In one embodiment the mandrel comprises a hollow tube with holes formed in the walls of the mandrel and a vacuum is drawn on the lumen of the mandrel during the compression procedure.

Figure 4:
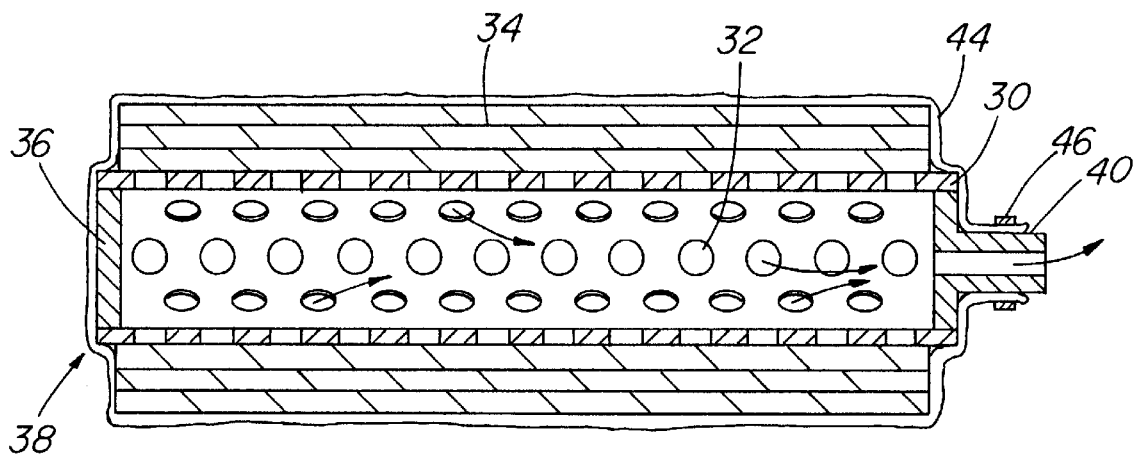
FIG. 4 is a sectional view of the purified submucosal covered mandrel wherein one end of the mandrel has been sealed and a vacuum is pulled on the opened end.

Alternatively, the compression of the purified submucosa may be achieved by continuously rolling the mandrel containing the wrapped matrix structure sheets in direct contact with another surface to provide a direct compression force. In addition, in one preferred embodiment, as shown in FIG. 4, the application of a vacuum can provide the sole compressing force for compressing the overlapped portions of the multiple strips of purified submucosa (vacuum pressing). In this embodiment a mandrel 30, formed as a hollow tube having a plurality of holes 32 formed in the wall of the mandrel 30 is covered with multiple layers of purified submucosa 34. The mandrel 30 is provided with a plug 36 for sealing the first end of the mandrel 38 and a terminal port 40 for withdrawing air from the lumen of the mandrel. The terminal port 40 is connected to a vacuum generating source and a vacuum is drawn on the lumen of the mandrel drawing air through the multiple layers of purified submucosa while compressing the layers against each other. A non-permeable layer can be wrapped around the multiple layers of purified submucosa (for example the mandrel can be placed within a plastic bag 44 that is sealed with a clamp 46 at the vacuum port) to provide a second surface that coacts with the mandrel to compress the multiple layers of purified submucosa between the second surface and the mandrel. A vacuum is applied, generally ranging from 14–70 inches of Hg (7–35 psi) and more preferably the vacuum applied is approximately 51 inches of Hg (25 psi). Optionally a heating blanket can be placed on top of the apparatus to heat the purified submucosa during the compression.

The multiple strips of purified submucosa are typically compressed for 12–48 hours at room temperature, although heat may also be applied. For example, a warming blanket can be applied to the exterior of the compressing surfaces to raise the temperature of the compressed matrix up to about 40° C. to about 50° C. The overlapped portions are usually compressed for a length of time determined by the degree of dehydration of the matrix. The use of heat increases the rate of dehydration and thus decreases the amount of time the overlapped portions of purified submucosa are required to be compressed. Typically, the layers are compressed for a sufficient time to produce a stiff but flexible material. Sufficient dehydration of the layers are also indicated by an increase in impedance of electrical current flowing through the matrix structure. When impedance has increased by 100–200 ohms, the purified submucosa is sufficiently dehydrated and the pressure can be released.

The compressed purified submucosa can be removed from the mandrel as a unitary compliant matrix construct. In one preferred embodiment shown in FIG. 5 the mandrel 50 is first wrapped with a removable porous ribbon material 52 before the sheets of purified submucosa are overlaid onto the mandrel. Preferably, the removable tape comprises a water permeable material that is resistant to tearing including a porous plastic or other material that does not adhere to purified submucosa or the mandrel. In one embodiment, the ribbon material comprises umbilical tape. The purified submucosa layers are then layered direct on the ribbon material and dried to form a unitary tubular construct. After drying the purified submucosa, the ribbon of water permeable material 52 is unwrapped from the mandrel 50 by pulling on the first end 54 and second end 56 of the water permeable material 52. (See FIG. 5) Removal of the ribbon of water permeable material 52 leaves a space between the purified submucosal construct and the mandrel, allowing for the removal of the construct from the mandrel.

The multi-laminate graft constructs can be formed to have substantially isotropic properties. These substantially isotropic (pseudoisotropic) grafts are prepared from at least two sheets of intestinal purified submucosa delaminated from both the tunica muscularis and the luminal portion of the tunica mucosa of a warm blooded vertebrate. Each of the sheets of intestinal purified submucosa are characterized as having a longitudinal axis corresponding to the predominant orientation of the collagen fibers in the purified submucosa sheets. The method of forming the pseudoisotropic graft constructs comprises locating a first sheet of purified submucosa on a the mandrel, overlaying said first sheet with at least one additional sheet of purified submucosa so that the longitudinal axes of each individual sheet of purified submucosa forms an angle of about 90° with its longitudinal axis of the outer sheet of the purified submucosa forming the heterolaminate graft.

Purified submucosa implants or constructs produced according to the present invention overcome the problem of leakage of fluid around suture holes of sewn matrix structures. The construction of two concentric tubes of purified submucosa wherein the sutured seams of the tube of the two tubes are offset relative to each other followed by adhering the two tubes of purified submucosa together ensures that the suture holes will not leak in the formed prothesis. Furthermore, the embodiments that utilize a cross-linking treatment to seal the seam of the first tube clearly do not have any perforations form in the tube wall and thus will not leak. The construct tubes produced according to the present invention exhibit an essentially seamless tube which will not leak fluid or require extra precautions associated with fluid efflux. This property is particularly important when the construct is to be used as a vascular graft, ureter replacement or as a shunt. The construct can be further manipulated (i.e. cut, folded, sutured, etc.) to suit various medical applications where the purified submucosal material of the present invention is required.

Other features and aspects of this invention will be appreciated by those skilled in the art upon reading and understanding this specification. Such features, aspects and expected variations and modifications are clearly within the scope of this invention.

EXAMPLE 1
Preparation of Tubular Purified Submucosa Graft Constructs

In one embodiment, the method of forming the construct comprises selecting a water permeable, hollow mandrel of appropriate diameter and spiral wrapping the mandrel with umbilical tape. Then the desired number of wraps of purified submucosa are applied wherein a "wrap of purified submucosa" is defined as a piece of purified submucosa wrapped 360° about the mandrel. Typically 1 or 2 wraps provide a burst strength of about 1000–2000 mmHg after fabrication as described below.

A sheet of purified submucosa is placed on a smooth flat surface with the mucosal side up. The tape-wrapped mandrel is laid on it with the long axis parallel to the long axis of the purified submucosa. A razor blade is then used to cut the purified submucosa parallel to the axis of the mandrel to form a linear edge for the purified submucosa. The purified submucosa is applied to the mandrel by a rolling motion with the desired number of layers (typically two) and an overlap region (defined by an overlap angle ($\theta$) of about 30 degrees extending between the two lateral edges of the purified submucosa) forms a tube of purified submucosa having a longitudinally extending seam.

After the mandrel has been completely wrapped, one end of the mandrel is closed and the interior of the purified submucosa-covered mandrel is connected to a vacuum pump. The vacuum causes atmospheric pressure to compress the purified submucosa layers and causes the glutaraldehyde to penetrate the entire thickness of the seam. The vacuum sealing/drying process is complete in about four hours typically.

After the drying/sealing treatment, the ends of the umbilical tape are grasped and pulled longitudinally. The tape unwinds easily under the purified submucosa tube which then slides off the mandrel easily. The result is a seamless tube that looks like a soda-pop straw.

Other sealant types, concentrations and wrapping techniques can be used. For example, spiral winding of a long, narrow strip of purified submucosa on the mandrel with an overlap is an option, followed by a spiral wrapping in the opposite direction as another. This will provide 4 layers of purified submucosa to support the internal pressure. This double helix could be combined with the wrap technique shown in FIGS. 3 and 5. In accordance with the present invention the purified submucosa can be wrapped onto the mandrel in a variety of different orientations. The one limitation is that no gaps should exist between the seams of overlapped strips. In preferred embodiments, seams formed by overlapped strips of purified submucosa should overlap by 0.5 to 3 cm and more preferably from 1 to 2 cm.

EXAMPLE 2
Spot Welding of Purified Submucosa Seams

In one embodiment, the seam of the wrapped matrix structure can be "spot welded" to ensure that the end piece does not come loose. In accordance with one embodiment, the seam is spot welded with a cross-linking agent such a glutaraldehyde. A Q-tip, moistened with X % glutaraldehyde (or other cross-linking or adhesive agent), is wiped along the overlap which is the seam. The value for X is about 0.1 to about 1.0%, more probably about 0.5%, but there is a relationship between the seam width, the glutaraldehyde concentration and number of turns that determines the bursting pressure.

In another embodiment, the seam of purified submucosa tube can be thermally spot welded to further seal the seam and bond the matrix structure into a unitary tube of purified submucosa. There are four factors that control the quality of a thermal spot weld applied to purified submucosa: 1) temperature, 2) force, 3) time of force application, and 4) the shape of the thermal welding tool. A pointed tool makes a weld with a hole. A flat tip makes no hole and a tip with a radius can make a small hole.

Using a small soldering iron with a temperature-calibrated tip, purified submucosa can be melted in discrete locations to form a "weld" point between two pieces of purified submucosa. By placing a specimen of purified submucosa on a glass plate (to avoid heat sinking), the warmed tip is applied to the purified submucosa to determine the temperature and time of application necessary to melt the matrix. Studies have been conducted on 1-cm wide strips of purified submucosa overlapped by 1-cm to determine the number of thermal spot welds required to hold two pieces of purified submucosa together. 5 spot welds in the 1×1 cm overlapping area produces a weld that is stronger than the force needed to break a single thickness 1-cm wide strip. A pointed tip produces a small weld with a hold; therefore the challenge is to identify the parameters that produce the strongest weld with the smallest hole.

To optimize the spot welding conditions, the following experiments are conducted. One cm wide by 10 cm long pieces of purified submucosa are utilized and fifty specimens will be fabricated and tested with three of the four variables (temperature, time, force and tip shape) being held constant and the one varied. In these first studies, the pointed tip will be used. The studies will be repeated with the 0.5 mm radius tip, then with a 1 mm diameter flat tip. The result will be the recipe for the strongest weld with the smallest hole, being measured with a microscope. We will also determine the break strength of selected specimens using the MTS machine.

b) Animal Model

The weanling rat model will be used to investigate the host response to spot welded purified submucosa strips. Anesthesia will be induced and maintained with metafane administered via face mask. The ventral abdomen will be clipped and prepared for aseptic surgery. Longitudinal skin incisions will be made in each abdominal quadrant. Then bilateral subcutaneous pockets will be created in the subcutis of each rat by blunt dissection. One 1 $CM^2$ test specimen will be placed subcutaneously within each pocket and secured in position with one 5-0 polypropylene suture to the underlying fascia. Skin incisions will be closed with a simple interrupted suture pattern with 5-0 polypropylene. Twenty-four rats will be used in this study.

After the elapsed time, euthanasia will be performed with intracardiac potassium chloride (at 1, 2, 4 and 8 weeks post implantation).

c) Morphologic Analyses

Samples removed for morphologic evaluation will be fixed in Trump's fixative for 24 hours, then placed in a phosphate buffer.

Specimens for light microscopy will be embedded in paraffin and sectioned to 2–3 $\mu$m. Section will be stained with hematoxylin and eosin (H&E) for overall morphology and VonKossa stain for calcification evaluation.

EXAMPLE 3

Purified Submucosa Tube Fabrication and Testing

The goal for this study is to produce grafts with an outer diameter of 5.0 mm. A multihole hollow mandrel of 4 mm diameter is spiral wrapped with non-overlapping umbilical tape. Then the two and one-half wraps of purified submucosa are applied to form a tube of purified submucosa and the overlapped portion will be fixed with glutaraldehyde in one group and with sutures in another group. A second sheet of purified submucosa will then be wrapped about the tube of purified submucosa and the opposing ends of the second sheet of purified submucosa will be sutured together. After wrapping, one end of the mandrel is connected to a vacuum pump and the other end of the mandrel is closed. The resulting vacuum in the mandrel causes atmospheric pressure to press the layers of purified submucosa together firmly and draws the moisture out of the purified submucosa, which requires about 24 hours.

After drying the layers of purified submucosa the ends of the umbilical tape are grasped and pulled longitudinally. The tape unwinds evenly under the purified submucosa tube which then slides off the mandrel easily.

e) Static Testing

Prior to burst testing, each purified submucosa graft will be soaked in 0.9% saline at 37° C. for 24 hours. The objective of this procedure is to determine the durability of the seams.

To determine the burst strength one end of the tubular purified submucosa graft is mounted to a fitting which will be used to apply air pressure. The other end of the tubular purified submucosa graft is closed with a suture and increasing air pressure is applied. A continuous recording of pressure versus time allows exact identification of the burst pressure. Our target is a burst pressure of 1000 mmHg or more. A successful fabrication technique is one that produces a burst, (at any pressure), without delamination. Tubular purified submucosa graft that pass this static test will proceed to pulsatile testing.

f) Pulsatile Testing

The critical period for a tubular purified submucosa graft is the first few weeks following implantation when it is in the initial stage of remodeling and is exposed to warm blood with a static (diastolic) and pulsatile pressure. During this time it is essential to know if the graft will retain its strength during early remodeling. Accordingly, we will perform pulsatile pressure testing with the graft constructs in saline at 37° C. A pulsating pressure of 200/150 mmHg will be used with a frequency of 1/sec. Testing will continue for 2 weeks after which the graft will be static burst tested.

EXAMPLE 4

Application of Tubular Graft as a Ureter

A multi-laminant construct is made by wrapping a perforated mandrel with 2½ turns of purified submucosa and vacuum-drying the construct for 8 hours. The construct is removed from the mandrel, rehydrated for 20 minutes and surgically implanted as a ureter prosthesis in a dog. The prosthesis conducts urine without leakage and heals into place to form a new ureter.

What is claimed is:

1. A unitary multi-layered graft prosthesis comprising a first sheet of a collagen-based matrix structure removed from a submucosa tissue source and having an endotoxin level less than 12 endotoxin units per gram, the first sheet having a first edge and a second opposite edge, formed in the shape of a tube, wherein the second opposite edge of the first sheet extends over the first edge of the first sheet to define a multiple layered overlapped region, wherein the layers in the overlapped region are fixed to one another; and a second sheet of a collagen-based matrix structure removed from a submucosa tissue source and having an endotoxin level less than 12 endotoxin units per gram, the second sheet having a first edge and a second opposite edge, wherein said second sheet is in adherent contact with the tube of said first sheet and the first edge and second opposite edge of the second sheet are joined together along the length of the tube without perforating the underlying tube of said first sheet.

2. The prosthesis of claim 1, wherein the first and second opposite edges of the first sheet are substantially parallel to one another.

3. The prosthesis of claim 2, wherein the tube comprises two layers and the multiple overlapped region comprises three layers.

4. The prosthesis of claim 1, wherein the multiple layers of said matrix structure in the overlapped region are fixed to one another by treatment with a cross-linking agent.

5. The prosthesis of claim 4, wherein the tube of said first sheet and the second sheet are fused to one another by compressing the matrix structures under conditions conducive to dehydration thereof.

6. The prosthesis of claim 4, wherein the cross-linking agent is glutaraldehyde.

7. The prosthesis of claim 1, wherein the multiple layers of the first sheet in the overlapped region are fixed to one another by sutures, the first edge and second opposite edge of the second sheet are joined together along the length of the tube by sutures, and the overlapped region is offset from the sutures formed in the second sheet of the matrix structure.

8. The prosthesis of claim 7, wherein the tube of the first sheet and the second sheet are fused to one another by compressing the matrix structures under conditions conducive to dehydration of the tissue.

9. The prosthesis of claim 1, wherein the matrix structure comprises purified tela submucosa removed from a submucosa source.

10. The prosthesis of claim 1, wherein the tube is formed to have the abluminal side of the sheet of the matrix structure on the exterior of the tube.

11. The prothesis of claim 1, wherein the matrix structure is purified.

12. The prosthesis of claim 11, wherein the matrix structure has a contaminant level making said purified structure biocompatible.

13. The prosthesis of claim 1, wherein the collagen-based matrix structure comprises small intestinal submucosa.

14. The prosthesis of claim 1, wherein the mature structure has a bioburden level less than 2 colony forming units per gram.

15. A unitary multi-layered graft prosthesis comprising a sheet of a purified collagen-based matrix structure removed from a submucosa tissue source and having an endotoxin level less than 12 endotoxin units per gram, the sheet having a first edge and a second opposite edge, formed in the shape of a tube, wherein the second opposite edge of the sheet extends over the first edge of the sheet to define a multiple layered overlapped region, wherein the layers in the overlapped region are fixed to one another.

16. The prosthesis of claim 1, wherein the collagen-based matrix structure comprises stomach submucosa.

17. The prosthesis of claim 1, wherein the collagen-based matrix structure comprises urinary bladder submucosa.

18. The prosthesis of claim 1, wherein the collagen-based matrix structure is uterine submucosa.

19. The prosthesis of claim 15, wherein the collagen-based matrix structure includes a material selected from the group consisting of small intestinal submucosa, stomach submucosa, urinary bladder submucosa, and uterine submucosa.

20. The prosthesis of claim 15, wherein the collagen-based matrix structure includes small intestinal submucosa.

* * * * *